United States Patent
Yorkston et al.

(10) Patent No.: US 10,136,871 B2
(45) Date of Patent: Nov. 27, 2018

(54) EXTREMITY IMAGING FOR ANIMALS

(71) Applicant: Carestream Health, Inc., Rochester, NY (US)

(72) Inventors: John Yorkston, Penfield, NY (US); William C. Wendlandt, Rush, NY (US); Peter A. Newman, Pittsford, NY (US); Carl R. Wesolowski, Alpharetta, GA (US); Douglas M. Csaszar, Webster, NY (US); Craig F. Hofmann, Fairport, NY (US); Donna K. Rankin-Parobek, Honeoye Falls, NY (US)

(73) Assignee: Carestream Health, Inc., Rochester, NY (US)

( * ) Notice: Subject to any disclaimer, the term of this patent is extended or adjusted under 35 U.S.C. 154(b) by 183 days.

(21) Appl. No.: 15/024,048

(22) PCT Filed: Oct. 9, 2014

(86) PCT No.: PCT/US2014/059850
§ 371 (c)(1),
(2) Date: Mar. 23, 2016

(87) PCT Pub. No.: WO2015/054466
PCT Pub. Date: Apr. 16, 2015

(65) Prior Publication Data
US 2016/0242719 A1 Aug. 25, 2016

Related U.S. Application Data

(60) Provisional application No. 61/889,190, filed on Oct. 10, 2013.

(51) Int. Cl.
*H05G 1/02* (2006.01)
*A61B 6/00* (2006.01)
(Continued)

(52) U.S. Cl.
CPC .............. *A61B 6/508* (2013.01); *A61B 6/032* (2013.01); *A61B 6/04* (2013.01); *A61B 6/107* (2013.01);
(Continued)

(58) Field of Classification Search
None
See application file for complete search history.

(56) References Cited

U.S. PATENT DOCUMENTS 6,735,274 B1 * 5/2004 Zahavi .................. A61B 6/032
378/15
7,036,169 B2 * 5/2006 Marshall .............. A61B 6/0421
378/208

(Continued)

FOREIGN PATENT DOCUMENTS

| GB | 2 028 053 | 2/1980 |
| JP | 2000-210280 | 8/2000 |
| WO | WO 2010/044844 | 4/2010 |

OTHER PUBLICATIONS

International Search Report dated Feb. 2, 2015 for International Application No. PCT/US2014/059850, 2 pages.

*Primary Examiner* — Hoon K Song

(57) ABSTRACT

An apparatus captures radiographic images of an animal standing on the apparatus. A base portion supports the standing animal and a moveable x-ray source is mechanically attached to the base portion. A digital radiographic detector is also mechanically attached to the base portion, and the x-ray source and the detector are configured to capture a radiographic image or a scan of at least one of the legs of the animal.

18 Claims, 16 Drawing Sheets

(51) Int. Cl.
*A61B 6/04* (2006.01)
*A61B 6/03* (2006.01)
*A61B 6/10* (2006.01)

(52) U.S. Cl.
CPC .......... *A61B 6/4007* (2013.01); *A61B 6/4085* (2013.01); *A61B 6/4435* (2013.01); *A61B 6/4452* (2013.01)

(56) References Cited

U.S. PATENT DOCUMENTS

| | | | |
|---|---|---|---|
| 7,492,862 B2* | 2/2009 | Bendahan | G01V 5/0041 378/195 |
| 2010/0098316 A1* | 4/2010 | Papaioannou | A61B 6/04 382/132 |
| 2010/0205740 A1* | 8/2010 | Tybinkowski | A61B 6/04 5/601 |
| 2010/0278300 A1* | 11/2010 | Yorkston | A61B 6/032 378/20 |
| 2011/0228901 A1 | 9/2011 | Yorkston et al. | |
| 2013/0089179 A1* | 4/2013 | Kenny | A61B 6/04 378/62 |

* cited by examiner

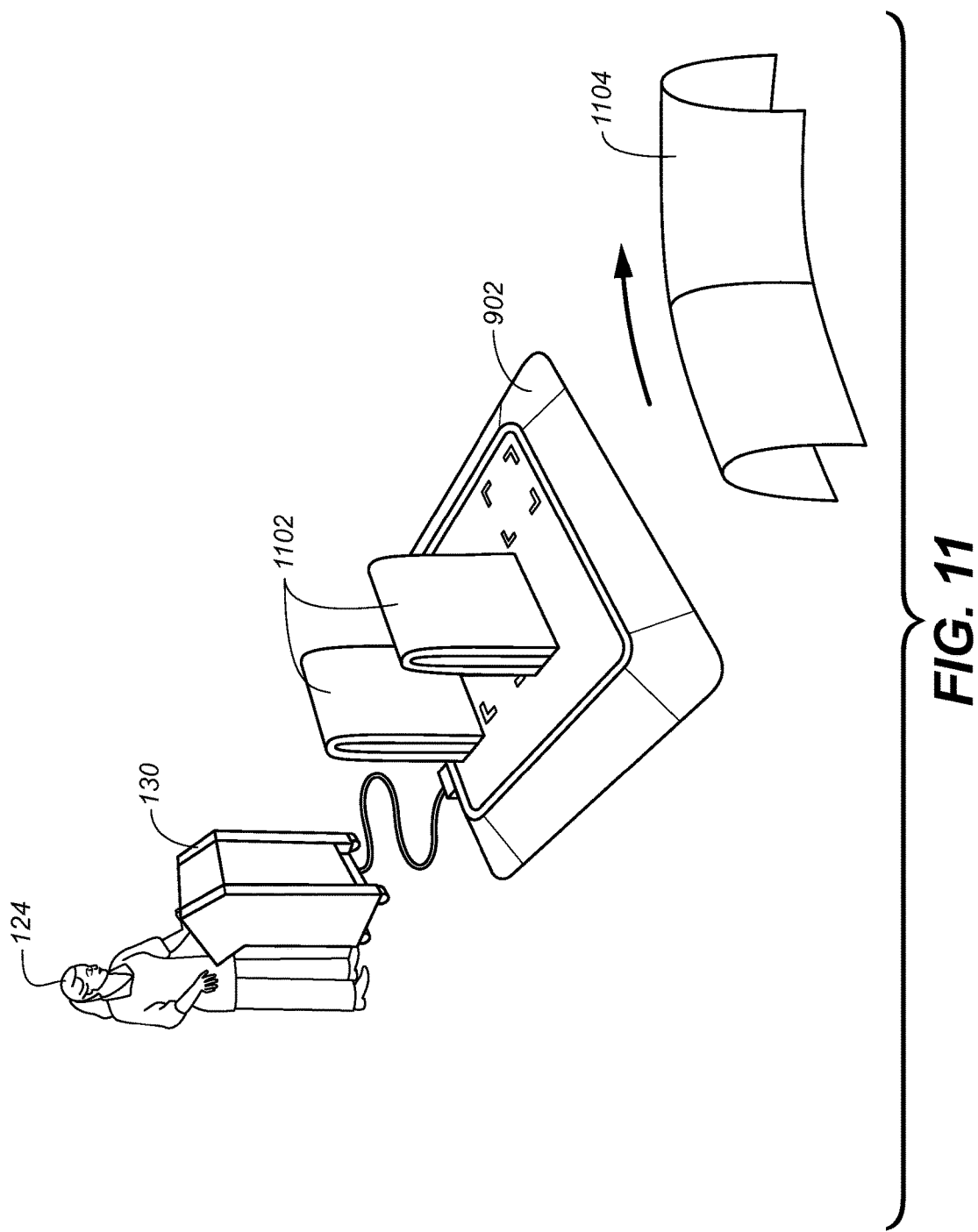

SECTION A-A

EXTREMITY IMAGING FOR ANIMALS

CROSS REFERENCE TO RELATED APPLICATIONS

This application claims the benefit of and is a U.S. National Phase filing of PCT Application PCT/US2014/059850 filed Oct. 9, 2014 entitled "EXTREMITY IMAGING FOR ANIMALS", in the name of Yorkston et al, which claims the benefit of (i) U.S. Provisional Patent Application No. 61/889,190 provisionally filed on Oct. 10, 2013, entitled "EXTREMITY IMAGING SCANNER FOR LARGE ANIMALS", in the names of Yorkston et al., all of which are incorporated herein in their entirety.

BACKGROUND OF THE INVENTION

The subject matter disclosed herein relates to radiographic imaging of animal subjects, in particular, to applications using Cone-Beam Computed Tomography imaging.

Cone-Beam Computed Tomography (CBCT) imaging would provide a useful tool for diagnosis and treatment assessment, planning, and tracking for an animal as the imaging subject. Certain exemplary CBCT imaging apparatus and methods described herein may address a number of practical challenges for performing CBCT imaging in veterinary applications that relate to considerations such as protection and cleaning of the equipment, shielding of technicians and practitioners during imaging, humane treatment of the animal subject in positioning and restraining the subject for imaging, and efficient use of imaging time and resources. Imaging apparatus embodiments may include a number of features for helping to guide the animal into position and keep the animal in position during imaging. Other considerations may include animal response and behavior in preparing for imaging, during an imaging scan, and afterward, with the expectation that animal behavior may be unpredictable.

The discussion above is merely provided for general background information and is not intended to be used as an aid in determining the scope of the claimed subject matter.

BRIEF DESCRIPTION OF THE INVENTION

Exemplary extremity imaging apparatus embodiments described herein may alternately be used for tomography imaging over a narrower range of angles than is sometimes used for CBCT imaging, for fluoroscopy, or for single-image radiography applications. It may be useful, for example, to obtain a number of radiography images of the same subject animal exposed at different angles. Images may be obtained by directing radiation through the subject animal at successive angular positions and capturing an image at each angular position. The image acquisition system may include a source of radiographic energy, a digital radiography (DR) detector, and related components that support orbiting of the source and detector over the range of angles, so that the source and detector may be substantially 180 degrees apart during the orbit, with the subject between them at every imaging position. The anatomical region of the subject animal may include a single extremity, such as leg or head. Alternatively, a pair of legs or other features may be simultaneously imaged.

An apparatus captures radiographic images of an animal standing on the apparatus. A base portion supports the animal which is standing, and a moveable x-ray source is mechanically attached to the base portion. A digital radiographic detector is mechanically attached to the base portion, and the x-ray source and the detector are configured to capture a radiographic image or a scan of at least one of the legs, for example, of the animal. An advantage that may be realized in the practice of some disclosed embodiments of the imaging system is convenient and portable radiographic imaging of animals at remote sites.

In one embodiment, an apparatus for radiographic imaging of an animal is disclosed. The apparatus comprises a support base to support the animal while standing on its legs. A moveable x-ray source is disposed within a source housing and is mechanically attached to the support base. A digital radiographic detector is mechanically attached to the support base. The source housing and the detector extend upward substantially perpendicular to, and above, a top surface of the support base, and are configured to capture a radiographic image of at least one extremity, such as the leg, of the animal.

In another embodiment, an apparatus for radiographic imaging of an animal is disclosed. The apparatus comprises a support base to support the animal standing on its legs. A moveable x-ray source and a digital radiographic detector are mounted on the support base. A rotatable orbital transport mechanism is attached to the support base, the x-ray source, and the detector, and revolves the detector and the x-ray source about one of the legs of the animal. The orbital transport mechanism positions the x-ray source at a first distance from a central axis and the detector at a second distance from the central axis, wherein the first distance is greater than the second distance.

So that the manner in which the features of the invention can be understood, a detailed description of the invention may be had by reference to certain embodiments, some of which are illustrated in the accompanying drawings. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

It is to be noted that the drawings illustrate only certain embodiments of this invention and are therefore not to be considered limiting of its scope, for the scope of the invention encompasses other equally effective embodiments. The drawings may be not necessarily to scale, emphasis generally being placed upon illustrating the features of certain embodiments of the invention. In the drawings, like numerals may be used to indicate like parts throughout the various views. Thus, for further understanding of the invention, reference can be made to the following detailed description, read in connection with the drawings in which:

FIG. 11 contains perspective views of an alternative exemplary imaging system for animals;

DETAILED DESCRIPTION OF THE INVENTION

Figure 1:
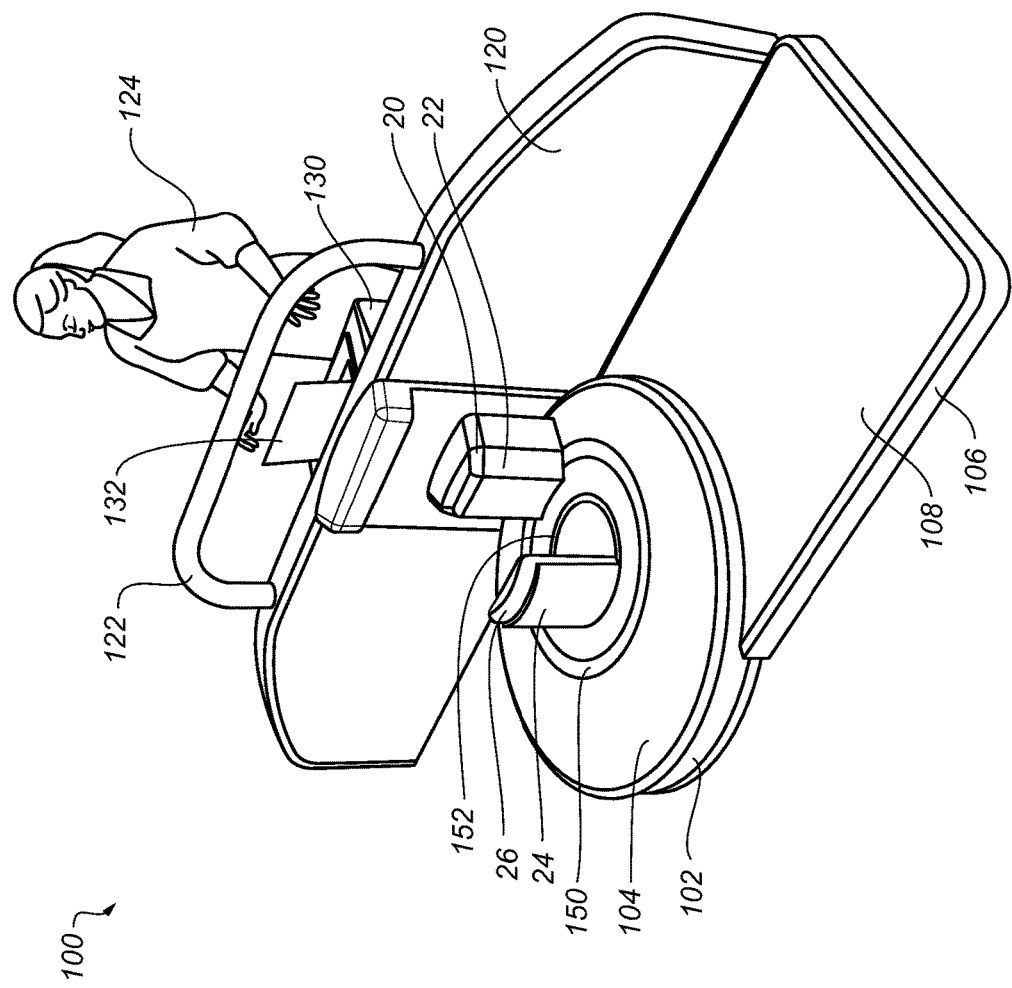
FIG. 1 is a perspective view of an exemplary imaging system for animals.

With reference to FIG. 1, there is illustrated an embodiment of an exemplary radiographic extremity imaging system 100. The extremity imaging system 100 includes a substantially circular support base 102 having a generally planar top surface 104 to provide a platform for supporting a subject animal. The support base 102 may be configured to be rotatable about a central axis through the center of the support base 102, as described herein below. Attached to the support base 102 may be a platform 106 having a generally planar top surface 108 to support an animal to be imaged. The platform 106 may be movable about the perimeter of the support base 102 to assist in positioning a subject animal for ease of imaging access to separate limbs of the animal. The top surface 108 of the platform 106 may be lower than the top surface 104 of the support base 102, as shown, or it may be at the same height or higher than the top surface 104 of the support base 102, depending on the desired level of the platform 106. The top surfaces 104, 108 may include a slip-resistant rubber mat or other suitable padding, hard surface, or cushioning for supporting an animal. The support base 102 base may be sized to support all four legs of a horse, for example, or only the forelegs or hind legs thereof (see e.g., FIG. 9). The support base 102 may have an adaptable arrangement of slots, mounting blocks, or other fittings to support permanent or removable structures that may help to guide the animal and help to shield equipment and personnel from animal movement, such as from kicking or stomping. The support base 102, as well as the platform 106 may include various shapes such as, but not limited to, the rounded design as shown in FIG. 1, as well as rectangular shapes described herein (see e.g., FIG. 7).

The extremity imaging system 100 may include a wall 120 which may include a radio-opaque material therein to provide a protective radiation shield for personnel or other animals near the imaging system 100 from radiographic energy emanating therefrom. The wall 120 may extend along the length of the support base 102 and the platform 106. The wall 120 may further include an attached rail 122 to be used for added support by an animal to be imaged or by an operator 124, such as those who may lead an animal into position for imaging on the extremity imaging system 100. Operative control of the extremity imaging system 100 may be programmed via a connected processing system 130 that includes a display 132, which may be controlled and operated via a user interface for receiving inputs from the operator 124.

The extremity imaging system 100 includes a radiation source 22 within a source housing 20 and a radiation detector 24 within a detector housing 26. For ease of reference, the radiation source 22 and its housing 20 may be referred to herein as the "source" and the radiation detector 24 and its housing 26 may be referred to as the "detector". The source and detector may be mounted to an orbital transport apparatus, at least a portion of which may be located within the base support 102. The orbital transport apparatus serves to revolve the source and detector about an imaging axis during an imaging scan of a subject animal that may be standing at least on the top surface 104 of the base portion 102, and may also be standing on the top surface 108 of the platform 106, as will be described herein below. Depending on the anatomical region of the subject animal being imaged, the forelegs of the animal may be positioned on the support base 102 while the hind legs may be positioned on the platform 104, and vice versa. Such positioning is exemplary only, and such positioning may depend on the size of the animal as well as on the size of the support base 102 and the platform 106. Thus, the orbital transport apparatus may be used to revolve the source and detector, if desired, selectively about a limb of a standing animal or other anatomical region of an animal positioned between the source and detector. For the sake of reference terminology, as used herein, the orbital transport mechanism may be said to "rotate" about an axis which causes the source and detector to "revolve" about the same axis.

To enable movement of the source and detector at the top surface 104 of the support base 102, the support base may include a moveable circular or curved portion 150 to which the revolving radiation source may be attached. Similarly, the support base may include a moveable circular or curved portion 152 to which the revolving detector may be attached. Alternatively, circular or curved slots may be formed in the top surface 104 to allow movement therethrough by the source and detector via an orbital transport apparatus positioned beneath the top surface 104 within the support base 102. Thus, the elements 150, 152, referenced in FIG. 1 may represent either moveable portions of the top surface 104, such as ring shaped portions, and they may represent slots through which the source and detector are attached to, and driven by, an orbital transport apparatus within the base support 102. Alternatively, the orbital transport apparatus may extend through such slots 150, 152 to secure and support the source and detector, respectively, at about the level of the top surface 104 to revolve the source and detector about a common axis. In one embodiment, the support base 102 may be large enough, with respect to its height, to allow storage of the source and detector within the support base 102 by lowering the source and detector through the slots 150, 152 into the support base 102. The source and detector may then be raised and emerge from below the top surface 104 through slots 150, 152. The source and detector housings may be raised manually, or by use of a motorized actuator, after the subject animal is moved into an appropriate position for imaging.

The orbital transport apparatus may carry the source about the subject animal's extremity to be imaged. In one embodiment, the orbit may be somewhat non-circular or curved. The orbit of the source generally defines a scan volume for the imaging system 100. The orbit may be centered or offset relative to a center of the support base 102. In one embodiment, the offset may be configured in coordination with the source's housing 20. The source may generally orbit about a central axis; its orbital path may be circular so that its radius about the central axis has a fixed value for any CBCT imaging sequence. The central axis defines a position wherein a subject animal's anatomical region, such as a limb, may be positioned for the imaging exposure sequence.

Using any of these alternative configurations, the source and detector may each be revolved a full 360 degrees, or may revolve only about 180 degrees plus a cone beam angle emitted by the source 22. Generally, movement of the source corresponds to a movement of the detector, thus, both the source and detector may be mounted to a common support structure for simultaneously revolving both during a scanning sequence, for example. Alternatively, the source and detector may be independently moveable to provide an option of adjusting a position of one or both for desired imaging schemes. According to an alternate embodiment of the imaging system 100, the support base 102 may be rotatable in turn-table fashion. The subject animal may be positioned on the support base and thus also rotates. The source and detector may remain stationary as the support base rotates during an imaging sequence.

Figure 2:
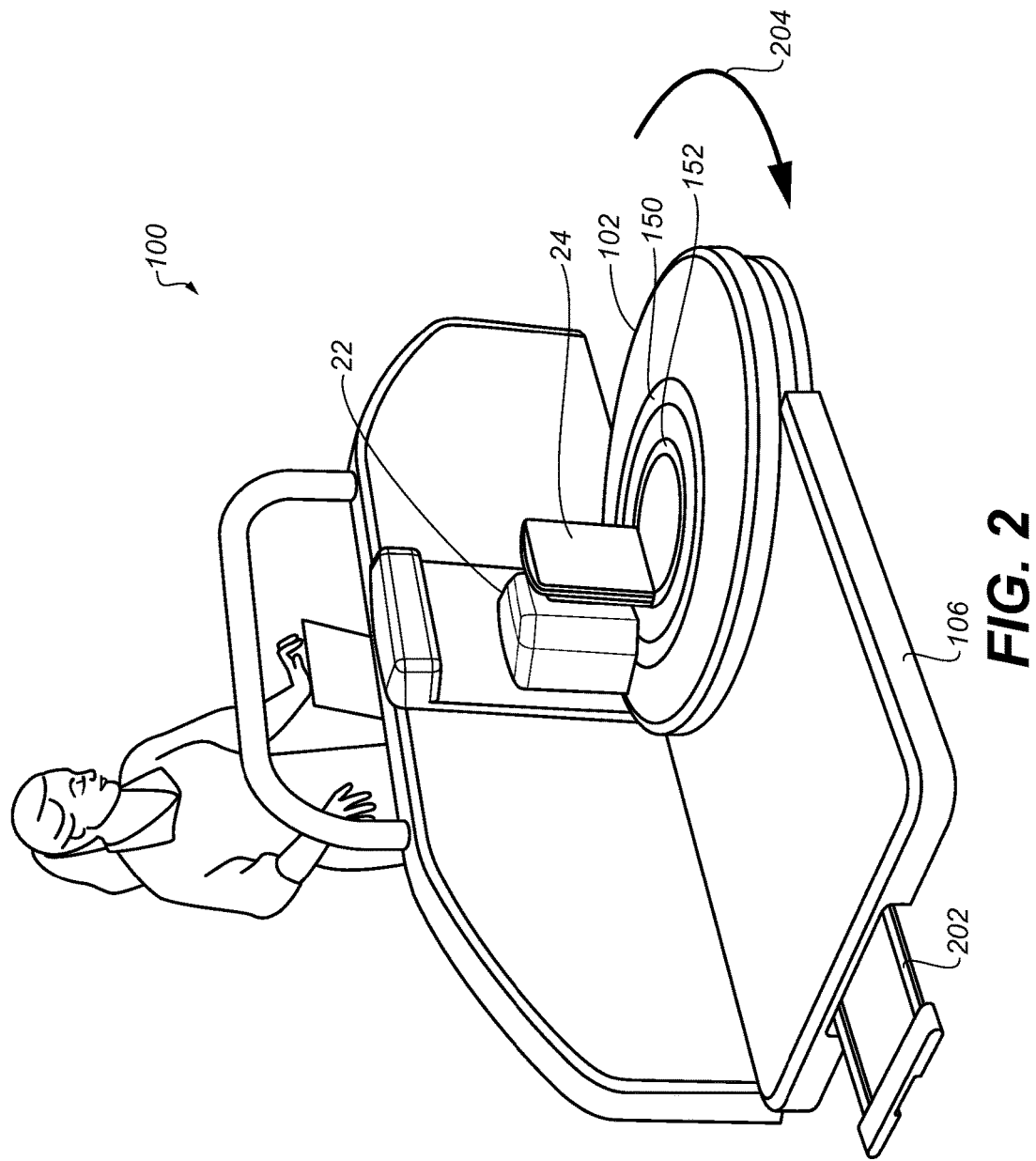
FIG. 2 is another perspective view of the exemplary imaging system for animals of FIG. 1.

FIG. 2 illustrates another position of the moveable platform 106 with respect to the support base 102, which may be revolved along the direction indicated by arrow 204, and which position may be desirable depending on an orientation of the imaging location wherein the imaging system 100 may be installed to allow easier ingress and egress of an animal onto the imaging system 100. The platform 106 may be motorized and include casters along a bottom surface thereof for revolving it into the position shown. A handle 202 may be provided to manually revolve the platform 106 to selected positions around the support base 102. Although FIGS. 1 and 2 illustrate positions of the platform 106 at opposite terminal positions, the platform 106 may be secured at any position between these terminal positions. The detector 24 is shown in FIG. 2 revolved along the slot, or ring, 152 into a position adjacent the source 24 and opposite the position of the detector 24 as shown in FIG. 1, which may be referred to herein as a neutral position, so that it does not impede comfortable movement of the animal onto the imaging system 100 prior to imaging exposures of the subject animal.

Figure 3:
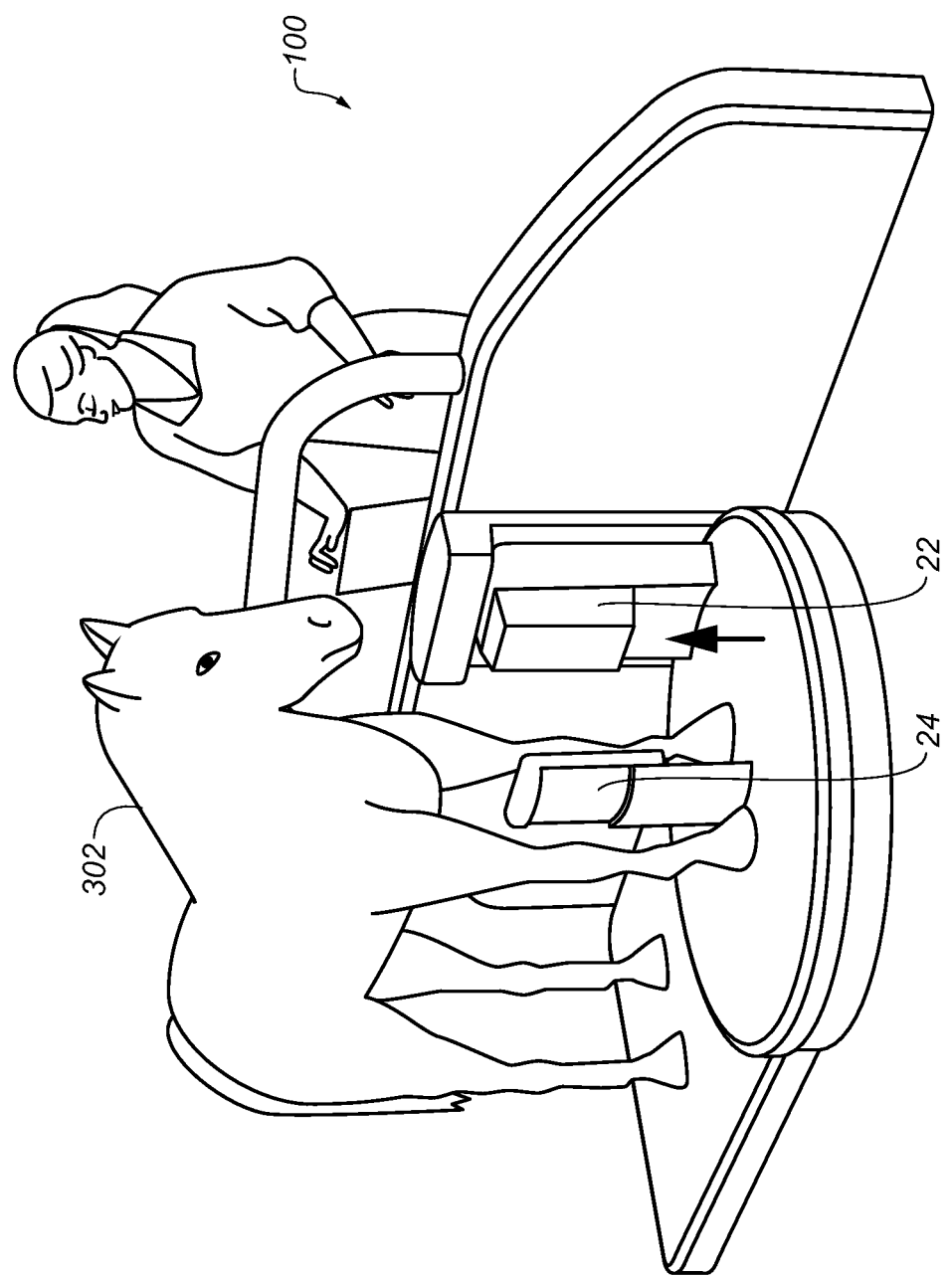
FIG. 3 is another perspective view of the exemplary imaging system for animals of FIG. 1 with a representation of a subject animal in position for imaging.

FIG. 3 illustrates imaging system 100 showing an exemplary subject animal 302, i.e. a horse, positioned for imaging by the source 22 and detector 24 of imaging system 100. As shown, the left foreleg of the subject animal 302 may be positioned between the source and detector for a single projection image exposure, or for a CBCT scan which may require activation of the orbital transport mechanism described herein for the source and detector, as the case may be. FIG. 3 also illustrates a feature of the source and detector which includes a mechanism for raising the source and detector in order to capture a radiographic exposure of the left foreleg of the horse 302 at a greater height than would be captured if the source and detector remain at their lowest position. This feature of the source and detector allows movement to any position between a lowest unraised position of the source and detector and a highest raised position thereof. Such movement may be implemented by a built-in motorized control or may be implemented manually such as by a detente mechanism for the source and detector having several stops between the raised and unraised positions. According to one embodiment, an adjustable manual motor control or a foot pedal motor control may include a fine-tuning capability for the height adjustment of the source and detector. In one embodiment, a single actuation of the control may automatically adjust the height of the source, the detector, or both, by a programmed amount (e.g., 1 cm). The source housing 20 may include a collimator for limiting an emitted radiation beam width of the source and changing or scaling a beam aspect ratio. One or more beam redirection devices may be employed to extend the angular range of the radiation source 22. Raising the source and detector does not interfere with operation of the orbital transport mechanism which may be activated for image capture at any raised position of the source and detector, or which may be simultaneously activated with the raising or lowering such as for a helical scan imaging sequence.

Figure 4:
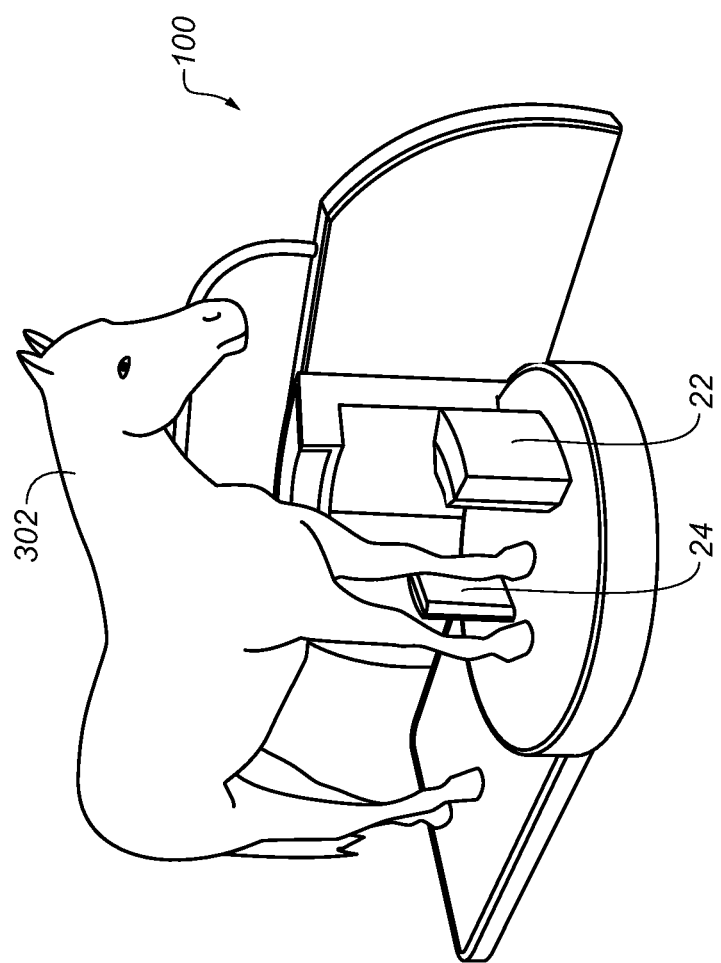
FIG. 4 is a perspective views of the exemplary imaging system for animals of FIG. 1 with a representation of a subject animal in position for imaging.

FIG. 4 illustrates imaging system 100 showing the exemplary subject animal 302 being imaged, whereby the source 22 and detector 24 of imaging system 100 are being revolved during a CBCT scanning sequence. As shown, the left foreleg of the subject animal 302 may be being imaged as the source and detector are revolved about that limb. The left foreleg of the horse 302 may be positioned in the axis of revolution of the source and detector and remains directly between the source and detector during the imaging sequence. As shown in FIG. 4, the source and detector may also be used for a single radiographic projection image exposure in the position shown, as desired.

Figure 5:
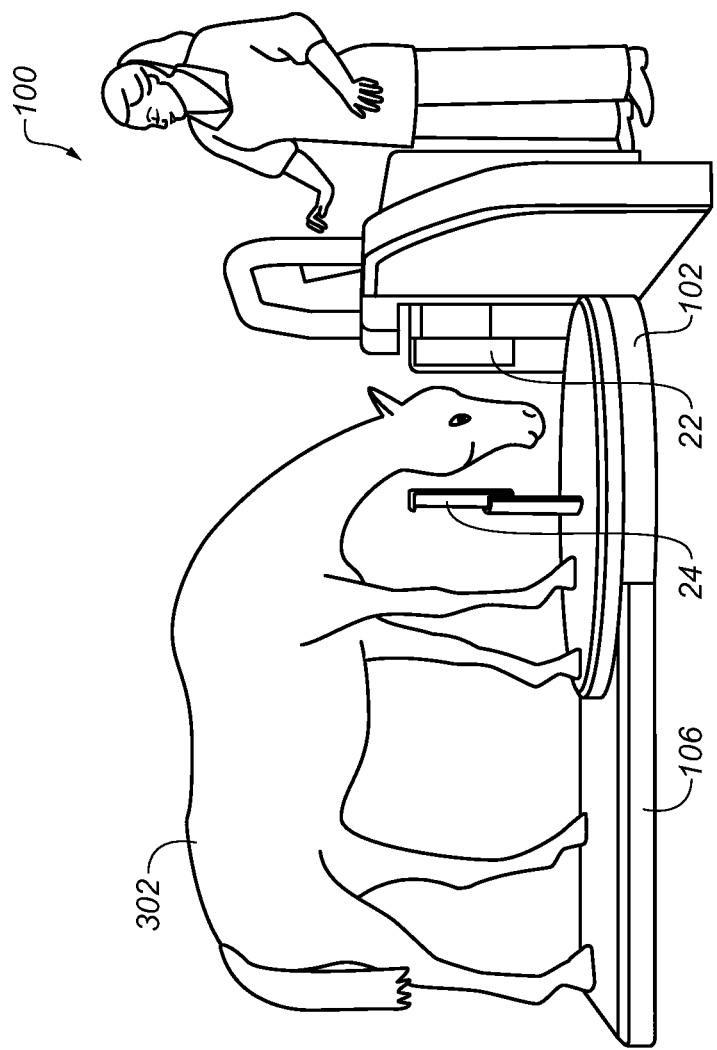
FIG. 5 is another perspective view of the exemplary imaging system for animals of FIG. 1 with a representation of a subject animal in position for imaging.

With respect to FIG. 5, the imaging system 100 is shown whereby the platform 106 has been moved to an intermediate position between the terminal positions with respect to the support base 102. This position of the platform 106 may be used for imaging the head of a subject animal, as shown, by placing its head between the source 22 and detector 24. The source and detector may be configured, such as increasing a space between them, to allow the animal to move its head to a lowered position therebetween. The top surface 104 of the support base 102 may be modified to include a recess in order to make room for the subject animals' snout, for example. In one embodiment, the source and detector may be mounted on a gimbal (e.g., universal joint) to be revolved, or maintained in a selected stationary position, for imaging the head of an animal. In one embodiment, the source and detector may be configured, e.g. programmed, to rotate up to about 90 degrees for imaging an animal's head. A leaning bar or surface against which the subject animal may apply its head with some amount of pressure helps to stabilize the head position during exposure. In one embodiment, a scan volume of the CBCT system may be increased (e.g., wider, longer) for head imaging. For hind leg imaging, handling of the subject animal for positioning may differ from front leg imaging. It may be useful to back the animal toward the source and detector components or to cross past these components and stop or restrain the subject at a given position. There may be some image processing differences based on particular aspects of animal imaging. One or more projection images may be rejected from the sequence due to excessive motion, for example. The range of imaging angles may be varied for different subjects, such as according to positions at which the animal remained still.

Although one platform 106, has been illustrated and described as a complementary structure for support base 102, more than one connecting platform may be coupled to the support base 102 to extend the top surface 104 thereof in order to support larger animals during an imaging sequence. As described above, the connecting platform may be rotated to a suitable angle about the support base 102, depending on the desired orientation of the animal for a specific radiographic exam. In one embodiment, the connecting platform 106 may include a ramp portion attached to support base 102 for ease of transporting a subject animal onto the imaging system 100. The platform 106 may alternately include a height adjustment mechanism to lift or lower the platform as well as the subject animal. Multiple attachable platforms may be provided to be added or removed from the support base 102, as needed. It may be advantageous to have the subject's front and hind legs on the same or a different level (height), as desired, for a particular imaging sequence.

Although the present invention may be not limited to a particular construction of the source 22, it may include a linear or a two-dimensional ("2D") array of radiation sources. In one embodiment, at least one of multiple sources may be removably (e.g., re-attachable) installed and, when detached, the remaining sources may be coordinated with the detector for projection radiography. Multiple radiation sources may be included to be separately energized, or energized as a group. The housing 20 of the radiation source 22 may provide shielding from the x-ray tube or other radiation emitter and related equipment. The source housing 20 may be manually removable and attachable from the base support 102 and, when replaced, rotates together with the source. The radiation source housing 20 may have a knock-down or breakaway feature, so that the housing and its source may be movable from an imaging position, in the event of kicking or other sudden, unpredictable responses of the subject animal. This provides a measure of damage protection for the source.

The detector 24 may include a digital radiography ("DR") detector that acquires images at a rate that may be commensurate with a corresponding imaging position of the source. The detector may comprise a digital flat panel detector having a generally planar, rigid, rectangular shape. The detector 24 may be configured to transmit acquired radiographic image data to the processing system 130 over a wired or a wireless communication link. According to embodiments of the present invention, detectors of different sizes may be usable in the detector housing. This enables use of detectors of different sizes or capabilities suitable for specific imaging applications. The detector may be removable from the support base 102 and may be revolvable toward or away from an imaging position. The detector is placed generally perpendicular to the top surface 104 of the support base 102, and the source may be aimed at the detector such that a central ray of the source is perpendicular to a plane of the detector. The detector may have a protective covering that may be used during positioning of the animal while setting up the imaging system 100 for radiographic exposures. The detector housing 26 may include a permanent cover or hood that may be translucent to x-rays, i.e. radiolucent, and resistant to damage from kicking. Such a hood over the detector housing 26 may be removed once the subject animal is in position for a radiographic exposure. In one embodiment, such a hood over the detector housing 26 may be affixed to the support base 102 in a stationary manner and used as a spacer to make sure enough room exists for the detector to pass between the legs of the animal and to prevent the animal from sensing or feeling the detector as it passes between the legs of the animal.

The processing system 130 may control operation of the imaging system components for setup, exposure control, scanning, including control of platform transport mechanisms, image data acquisition, image processing, and presenting image data on the display 132. Image processing functions may be partially or mainly performed by a processor in the detector, prior to transmission of the acquired image data to the processing system 130. An operator/user interface on the display 132 may provide utilities for entry of operator commands. In one embodiment, multiple displays may be provided to allow animal handlers or veterinary personnel to view instructions for setup as well as results, such as with images displayed as acquired. Images may be refreshed at a lower rate than the acquisition rate, but sufficient for determining whether or not the appropriate anatomy of the subject animal is being imaged. The operator interface may be provided on a movable, free-standing, processing system console that includes the display (see e.g., FIGS. 7-9). Wired or wireless connection of the console to the detector and source may be available. Cabling may extend into the support base 102 for interconnection of the detector and source components to the processing system 130 as well as for transmission of image signals, power, and data to control the detector and source orbital transport apparatus. According to an alternate embodiment, cables may be tethered to one or more components mounted on or internal to the support base 102 from above or from alongside the imaging system.

The orbital transport apparatus may be configured to allow the source to move independently of the detector during setup of the imaging system 100, such as during positioning of the subject animal for imaging. The detector portion of the orbital transport apparatus revolves the detector about the subject animal extremity to be imaged. In one embodiment, the detector path may be configured to travel around at least a portion of the scan volume. In one embodiment, the source revolves along a circular path having a diameter greater than the detector's path. A center of the source and detector paths may coincide with a center of the support base 102 or they may be offset. As with the source, the detector may generally orbit about a common central axis so that its radius has a fixed value for any CBCT imaging sequence.

Embodiments of the extremity imaging system 100 may include portable configurations to allow ready transport to on-site imaging locations such as at a stable, veterinary clinic, or other imaging site. A trailer-mounted version of the imaging system 100 may be built onto a trailer that may be driven or hauled from site to site. A ramp or other device may be used to lead the subject animal onto the trailer for an imaging exam. A depression or well may be provided in the trailer. The surface of the trailer bed may provide the functions of the support base, as noted previously. With the trailer arrangement, the imaging system's support base or its components may be lowered, such as to below a level of the floor of the trailer, to allow imaging of hoofs and other lower areas. For the trailer-mounted version, sides of the trailer may lift out or be hinged to increase the platform area available. The horse or other animal may climb up onto the trailer. A number of supporting components such as walls, railing, shields, lead aprons, and the like may be configured on and around the support base in a mobile scanning apparatus. Vent holes and other features may be provided in the trailer base for facilitating removal of solid and liquid waste, water, and cleaning fluids. Embodiments of the imaging system 100 may be transported on a trailer and unloaded from the trailer for set-up at a remote imaging site.

According to an embodiment of the present invention, the subject animal may be positioned such that its leg, or other anatomical region to be imaged, may be placed in a target location, such as the central axis A (FIGS. 15 A-B and 16 A-B) while the source and/or the detector are moved to a neutral position. After positioning the subject animal, the source and detector may be then moved into an imaging position and, over a range of angles, controllably orbit the leg or other anatomy to be imaged. A scanning sequence may be executed by moving the source and detector in either clockwise or counter-clockwise motion about the subject animal's anatomy. Helical or spiral imaging patterns may also be provided, wherein the source and detector are activated to revolve about the subject animal's extremity while simultaneously raising, and/or lowering, the source and detector as described herein. A helical scan may be used, for example, for long-length imaging of a limb of the subject animal. In one embodiment, dual scans at different height positions of the source and detector may be performed back to back, and then projection images or reconstructed 3D volume images may be combined together such as by digital stitching. According to an embodiment, the operator may designate, i.e., program, an appropriate starting and ending angle for a particular scan sequence. Thus, for example, where it may be challenging to position an animal properly, the scan operation of the system may be adapted to compensate to generate the desired radiographic image. In one embodiment, for example, the detector imaging path may cover 360 degrees so that a particular exposure arc (e.g., 180 degrees plus cone angle) may be selected anywhere within the 360 degree range. In one embodiment, the selected detector/source path may provide that any moving part (e.g., the detector) that will become visible to the horse must travel from a position under the horse out toward the front of the horse to help prevent startling the animal (in contrast with approaching the horse from the front). It may be desirable to obtain images over a range of angles where the subject animal may be most stably positioned in a non-standard stance. The source and detector may be programmed to start imaging at a particular angle that may be most favorable, given these conditions. This may be a particular advantage for tomography and other imaging modes.

In a method of operating the imaging system 100, an exemplary sequence of method steps will now be described.
1. Lead and position the subject animal for image acquisition. Various features may be provided to help guide the horse or other subject animal into position. Either or both the detector housing and the radiation source housing may be movable to a neutral position to while the horse or other animal is guided into place.
2. Optionally place protective shields, aprons, curtains, or other coverings into place to hide or disguise the imaging components from the animal.
3. Position the extremity to be imaged between the source and the detector or move the source and detector in position about the extremity of the animal. This step may involve using various devices such as bars, a tunnel, barriers, or other components into place, where these devices constrain movement of the subject extremity. In one embodiment, a scan gate may be placed between the horse's imaged legs to (i) ensure there is existing room for the detector and/or (ii) reduce the likelihood that the detector contacts the horse's imaged leg during the scan or image exposure sequence.
4. Execute the image exposure sequence, as described previously, by activating the source and detector.
5. Restore the source and detector to interim positions after removing the scan gate, if any.
6. Guide the animal away from the imaging system.

Figure 6:
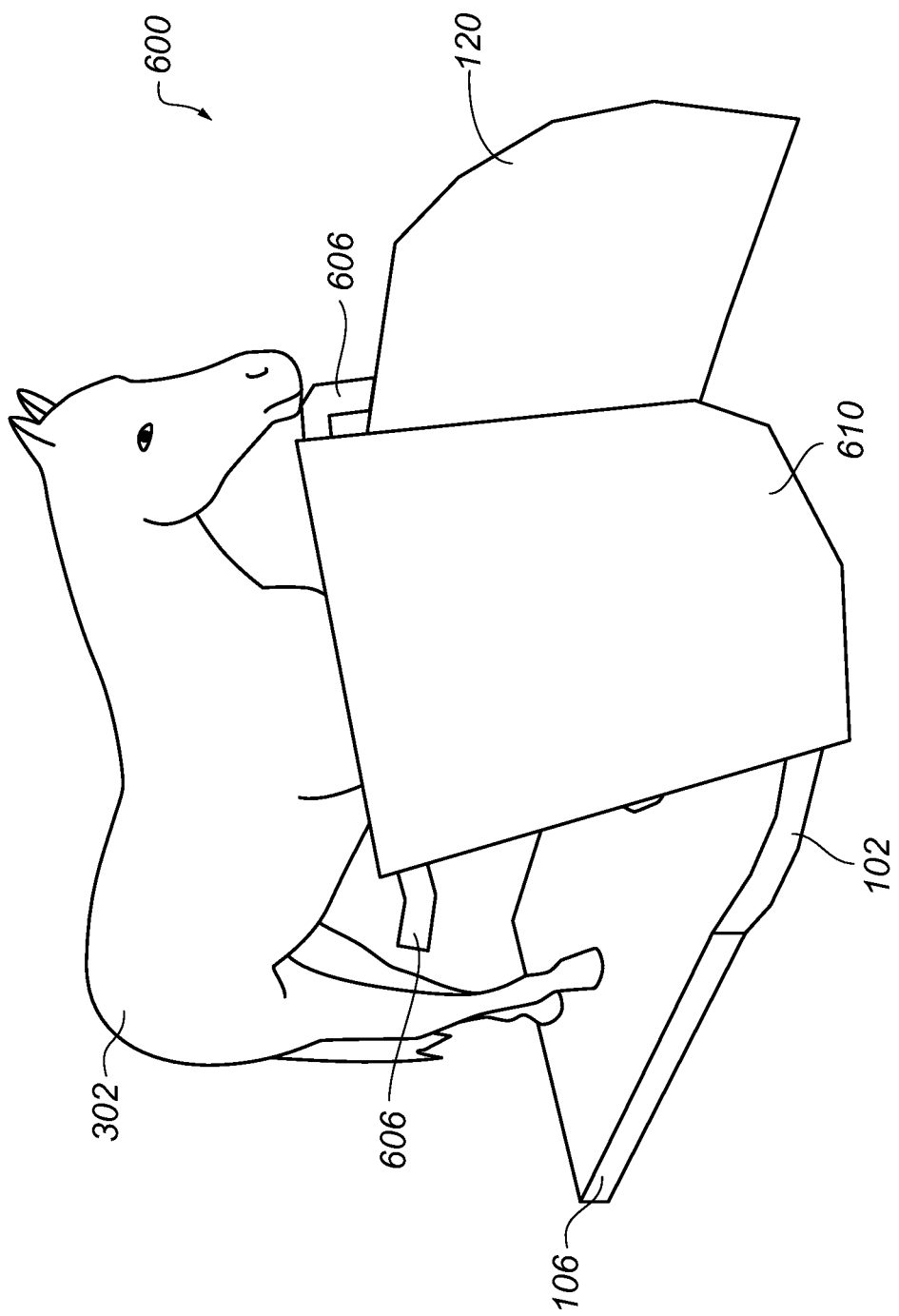
FIG. 6 is a perspective view of an alternative exemplary imaging system for animals with a representation of a subject animal.

FIG. 6 illustrates an alternative imaging system 600 including a protective apron 610 comprising a radio-opaque material for shielding radiographic energy generated by the source. The imaging system 600 may include a rail 606 that is rotatable from a position along a wall 120 to a position in front of the subject animal 302, as shown, to provide a support for the protective apron 610, which may be draped over the rail 606. The rail 606 may also be used to help maintain the subject animal in a correct position on the support base 102 and platform 106 during an imaging sequence.

Figure 7:
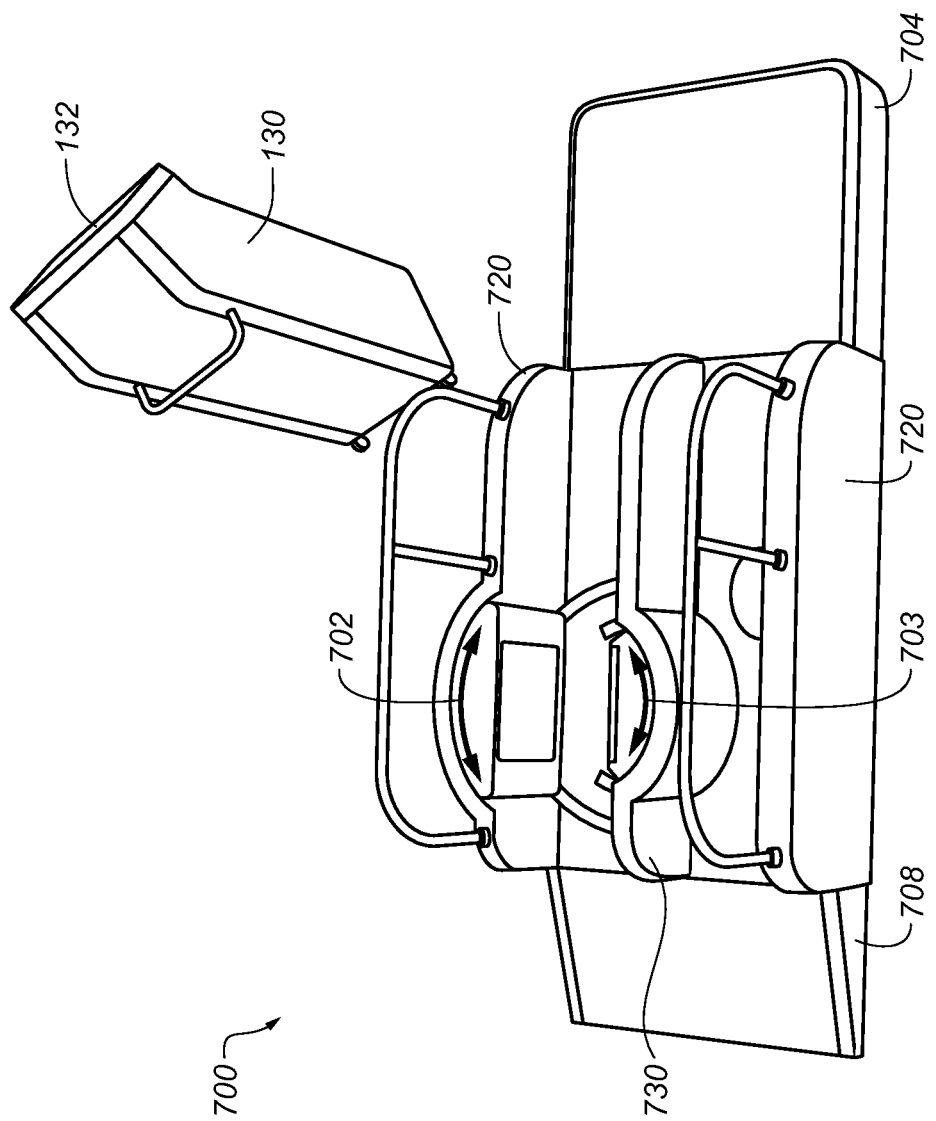
FIG. 7 is a perspective view of another alternative exemplary imaging system for animals.
Figure 8:
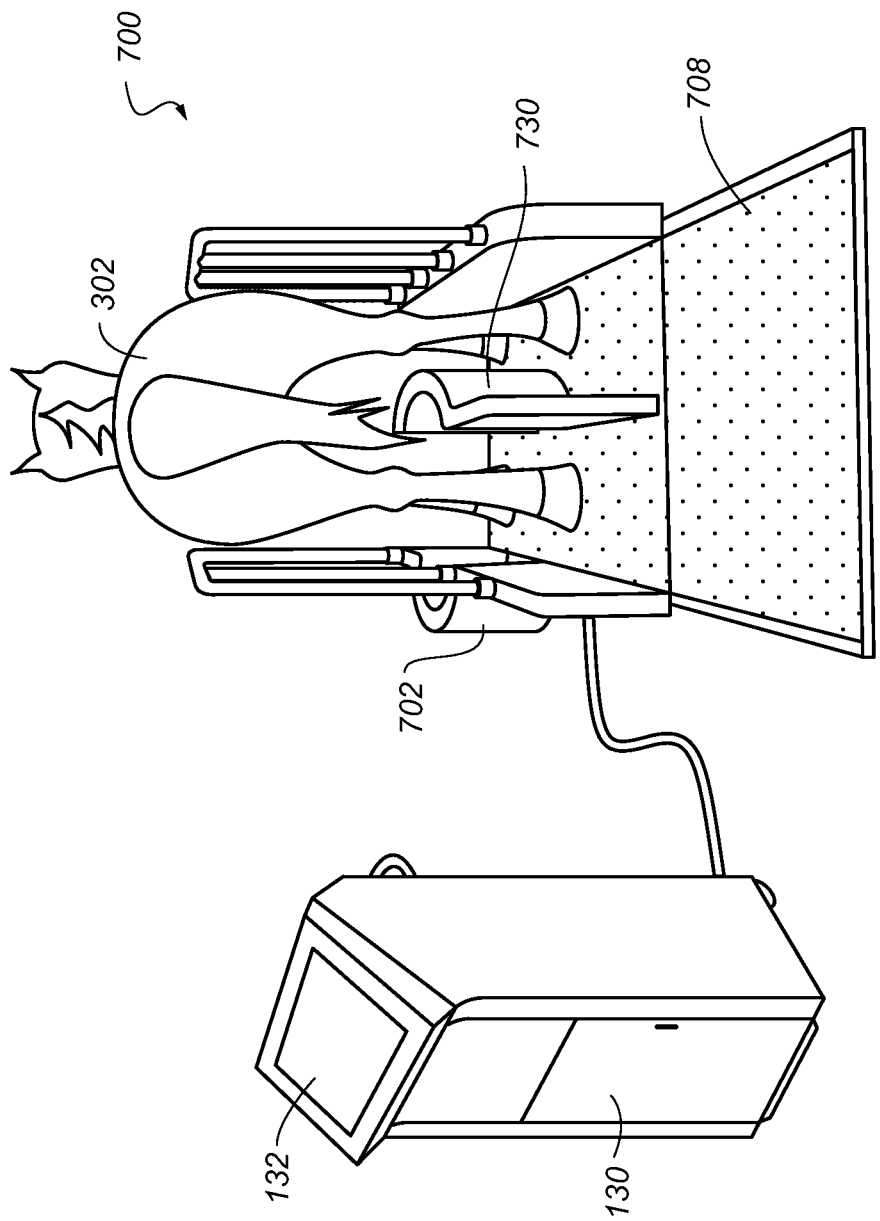
FIG. 8 is a perspective view of the exemplary imaging system for animals of FIG. 7 with a representation of a subject animal in position for imaging.

FIGS. 7-10 illustrate alternative embodiments of the imaging system 100. In the embodiment of FIG. 7 the imaging system 700 may comprise an intermediate structure 730 may be provided for straddling by the subject animal. This structure 730 may be fitted between the animal's legs after the animal is guided between the guide rails, or walls 720. The straddled structure may be positioned by raising it through the support base or platform 704. The tunnel, bridging, or other straddled structure may have a curvature to more easily adapt to the subject anatomy or to conform to the orbit 702, 703, of the underlying source or detector. A ramped incline portion 708 may be attached to the platform 704 to assist walking the subject animal into the imaging system 700. FIG. 8 illustrates a perspective view of the imaging system 700 having a subject animal 302 in position for imaging therein.

Figure 9:
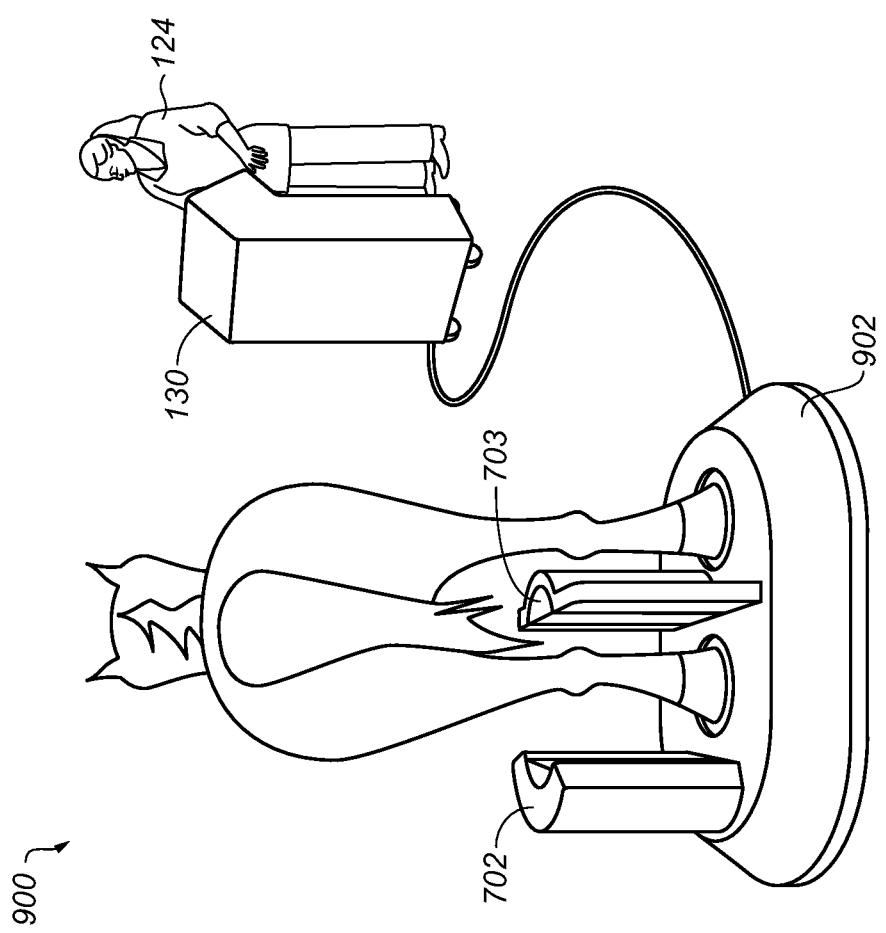
FIG. 9 is a perspective view of an alternative exemplary imaging system for animals with a representation of a subject animal in position for imaging.
Figure 10:
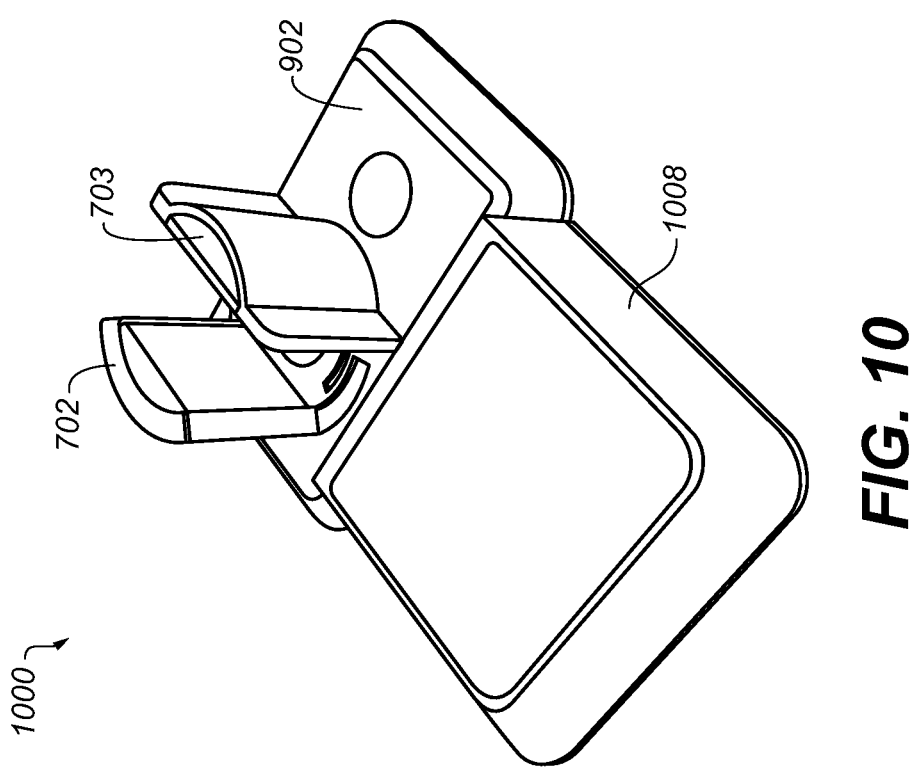
FIG. 10 is a perspective view of an alternative exemplary imaging system for animals.

FIG. 9 illustrates an alternative embodiment of the imaging system 100. In the embodiment shown, the imaging system 900 comprises a smaller, shortened support base 902. In this exemplary embodiment, the hind legs of the subject animal are positioned on the support base 902, one of which is positioned between the source 702 and detector 703, and are supported in a higher position than its forelegs. Conversely, the forelegs of the subject animal may be supported at the higher position if a foreleg imaging exposure is desired. FIG. 10 illustrates an alternative embodiment 1000 of the imaging system 900 shown in FIG. 9, whereby an extension platform 1008 may be attached to the shortened support base 902 to provide a level support structure for the subject animal.

FIG. 11 illustrates hood structures 1102 which may be used to cover the source and detector to conceal their movement during imaging from the subject animal, which may otherwise be startled. According to an extendible embodiment 1104 of the hood structures, a tunnel may be formed using curved sections that telescope along the transport path circumference of the source and/or detector during positioning or during imaging of the subject animal. Extending the tunnel over the extent of the transport path may be done manually or by an actuator. A spacer (e.g., foam) or other spacing tool may be used to check extremity spacing during positioning of the animal. This may include a foam member that may be placed between the legs, such as near the chest, to check against possible interference of the leg with the detector transport path. In one embodiment, the spacer may be elastically held in place.

Additional features may be provided for making the subject more secure and less likely to be frightened and kick or otherwise become too agitated to remain still during imaging. These may include visual stimuli or blinds; music, white noise or other audible stimulus; fans or other external devices for moving air past the animal; smells; liquids; heat, cold, or other stimuli. In other embodiments, the sound, white noise or music may be selected to begin at a first level (e.g., low or inaudible to the horse) and end at a second level sufficient to cover or be louder than the CBCT imaging system (e.g., moving sounds of the source/detector and noise caused by the radiation source/generator). In one embodiment, an intermediate level of noise may be used to cover the general operating sound of the CBCT apparatus when not imaging. For any stimulus, variation in strength or intensity may be used to provide a more natural distraction for the animal, such as increasing or changing sound volume or fan speed, for example.

Figure 12B:
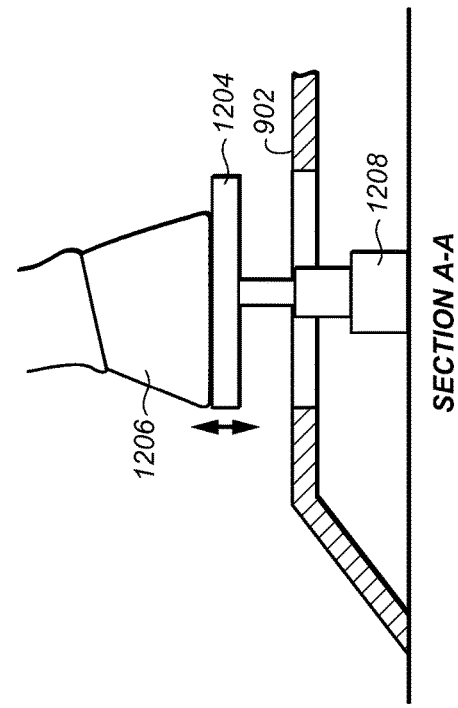
FIG. 12B is a cross-sectional view along section A-A of the pedestal of FIG. 12A for positioning a foot of an animal to be imaged.
Figure 12C:
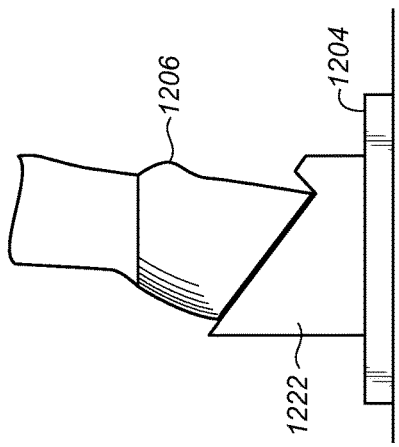
FIG. 12C is a side view of an alternative exemplary pedestal for positioning a foot of an animal to be imaged.
Figure 12A:
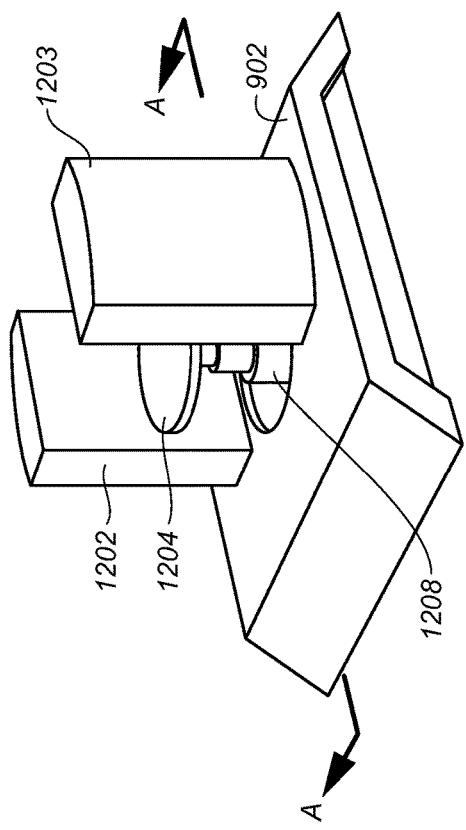
FIG. 12A is a perspective view of a pedestal for positioning a foot of an animal to be imaged.

With respect to FIGS. 12A-14, in particular, FIGS. 12A-C, imaging a hoof 1206 or lower leg portions of a subject animal may be improved using a pedestal 1204 or other device to position the hoof 1206. The pedestal 1204 may be formed to include an angled support 1222 to suit the shape of the hoof. A hydraulic lift 1208, worm gear, or lead screw, for example, may be connected to a bottom of the pedestal 1204 and raised to elevate the pedestal 1204 to a desired imaging position. The pedestal 1204 may be located in the support base 102 between the source and detector in the embodiments described hereinabove, or it may be located in the shortened support base 902 between the radiation source 1202 and the DR detector 1203, for example. In one embodiment, the hoof may be placed upon, or secured to, a pedestal 1204, which, in turn, may be coupled to the support base 902. A control at the base of the pedestal allows the technician to raise or lower the pedestal as needed.

Figure 13:
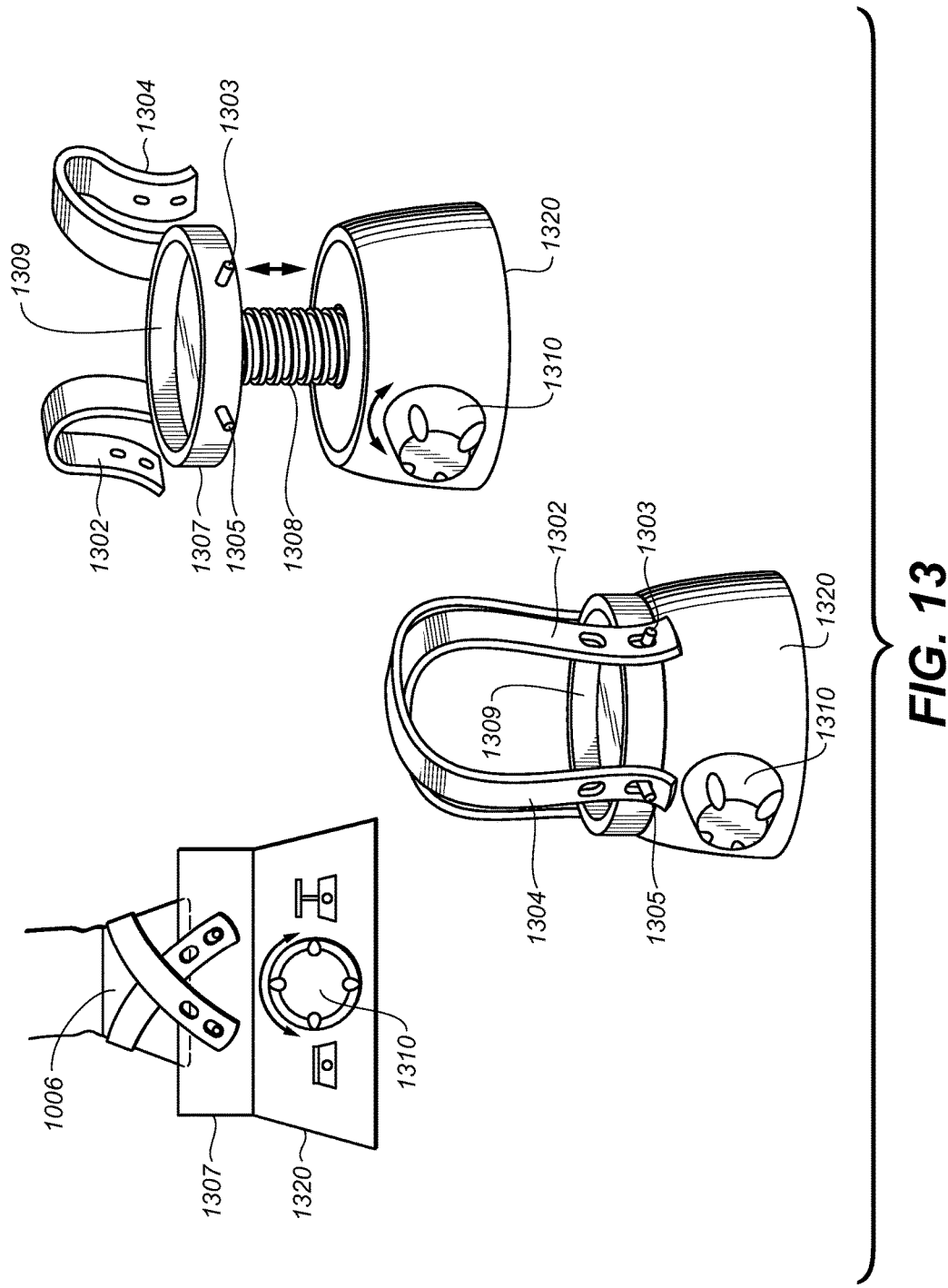
FIG. 13 contains views of an exemplary foot restraint useable with the pedestal of FIG. 12A.
Figure 14:
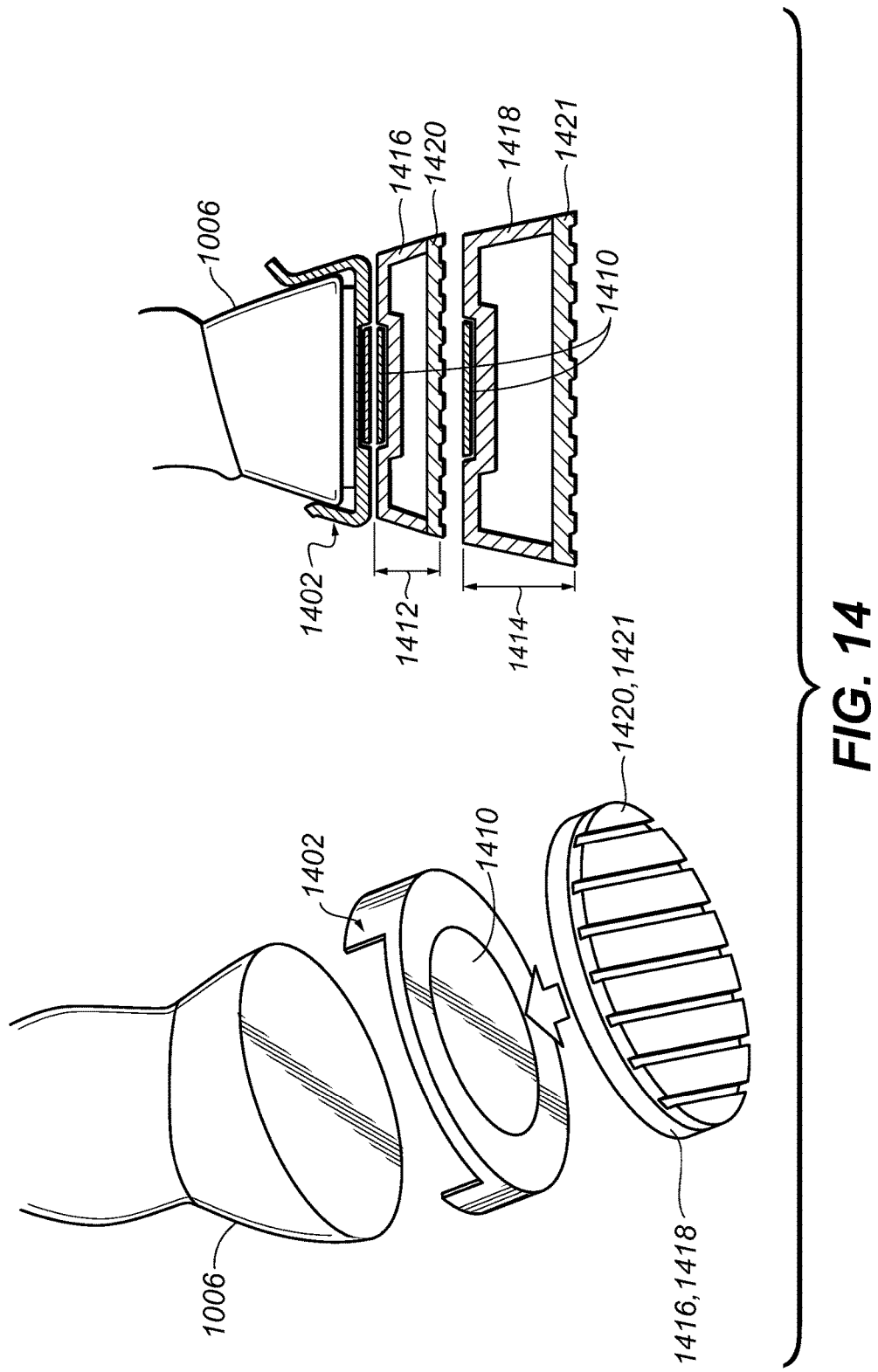
FIG. 14 contains views of an exemplary magnetic foot restraint for positioning a foot of an animal to be imaged.

With respect to FIGS. 13-14, a clamp 1402, straps 1302, 1304, or other device may alternately be used to constrain the hoof 1006. The hoof may be placed in a pedestal 1307 having a recessed cavity 1309 to receive the hoof. Straps 1302, 1304, having holes therethrough may be wrapped around the hoof and affixed to securing pins 1303, 1305, respectively. A height of the pedestal 1307 may be adjusted using a screw 1308 attached to the bottom 1320 of the pedestal 1307 or by turning a knob 1310 configured to activate a mechanism in a base portion 1320 of the pedestal 1307. Alternately, a clip-on clamp-type "shoe" 1402 or other insert that flexibly attaches to a hoof 1006, may have a magnetic portion 1410 for attraction to a wearable block 1416, 1418. Anti-slip material 1420, 1421 attached to blocks 1416, 1418, respectively, such as rubber may be provided. The blocks may be formed in various thicknesses (heights) 1412, 1414, so that the hoof 1006 may be positioned for imaging as desired. The height of the scanning components, radiation source and detector, may be adjusted according to the pedestal elevation of the hoof. Where the scanning components may be moved to below the top surface of the support base 102, 902, the hoof may be placed directly on the top surface. In one embodiment, the detector may be positioned below the top surface 104 of the support base 102 to orient the detector lower edge below the imaged hoof. In one embodiment, a surface configuration of the support base 102, 902 may be made from X-ray transmissive material to allow imaging by the detector when recessed into the support base 102, 902.

Certain exemplary imaging system 100 embodiments may provide the platform and support base having at least two heights, a first lower height for standard imaging and a second higher height for hoof imaging. For the second height, intermediate height additional platform may be used to allow the horse to reach the second higher height, which may be higher than a horse may step. Alternatively, a ramped additional platform may be used to get the horse to the second higher height. In one embodiment, at the second higher height configuration, the platform and support base outside the source path may be at the second higher height, but the source, detector and an inner region remain at the first lower height. In one exemplary second higher height configuration, an area inside the source path may be filled with: (i) a first radiation transmissive ring coupled to rotate with the source, (ii) a second intermediate radiation transmissive ring coupled to rotate with the detector, and (iii) an inner radiation transmissive region to support the hoof. In an alternative embodiment for the source, the source may be configured to move/extend to a height above the detector, even with the inner region or above the inner region, and may be configured to shift to one or more angled orientations to improve alignment with the detector (e.g., through the inner region). The detector and source may be both elevated for knee and hock imaging, as shown in FIG. 2. Height may be manually adjustable or adjustable using a motor or other actuator in detector housing or radiation source housing.

Figure 15A:
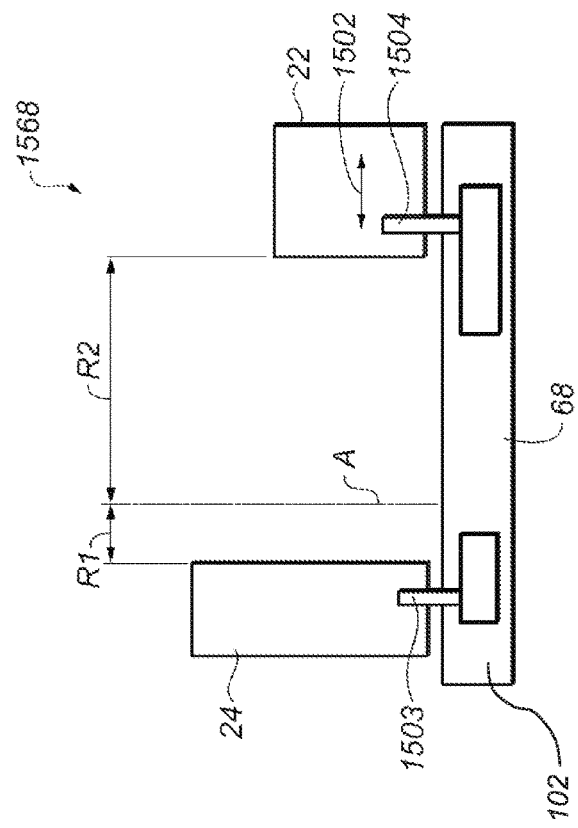
FIGS. 15A-15B are schematic diagrams of an exemplary source and detector orbital transport apparatus.
Figure 15B:
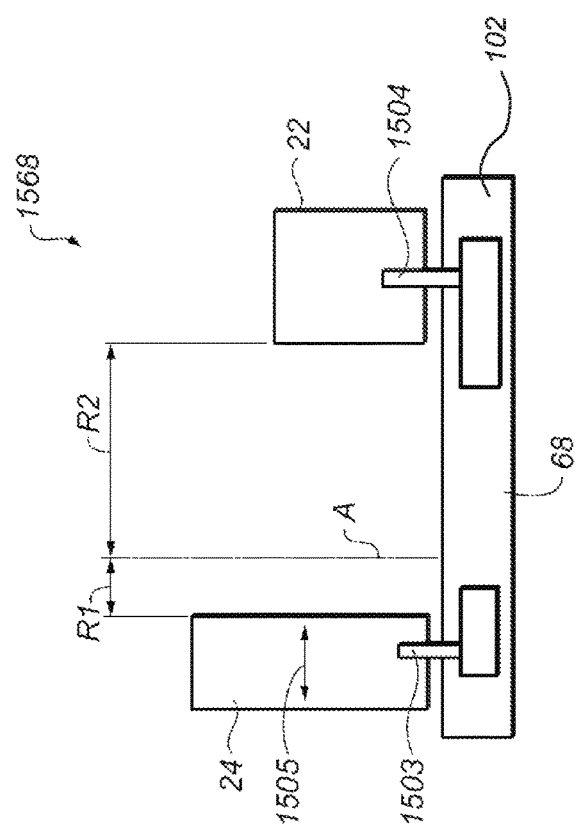

With respect to FIGS. 15A-B, the orbital transport apparatus 1568 may be configured to adjust a radius of the source's orbit R2 over a range to suit different imaging conditions. Thus, for example, a configuration by which the source 22 may be coupled to the orbital transport apparatus 1568 allows a change to the source's orbital radius R2. This change in radius R2 may be accomplished in a number of ways, such as by an adjustable offset indicated by arrow 1502 using a threaded connector 1504 that protrudes through the source slot 150 in the support base 102, for example. This adjustment may be manual, or automatic such as based on operator selection of an exam type, which selection may be input via a user interface presented on the display 132. It may be preferable to maintain the source radius R2 greater than the detector radius R1. For coordinated scan operation, the orbital transport apparatus may be configured as a unitary structure supporting and transporting the source 22 and detector 24 simultaneously. This allows the source to face the detector at a diametrically opposed 180 degree angle for imaging over a range of imaging angles, having the subject animal positioned between the source and detector. One or more motors or other actuators, which may include a manual actuator, may be used to move both the source and detector at an appropriate speed for an imaging scan. Similarly, the radius of the detector orbit R1, may also be adjusted over a range to suit different imaging conditions, by using a threaded connector 1503 to adjust a position of the detector 24 as indicated by the arrow 1505.

Figure 16A:
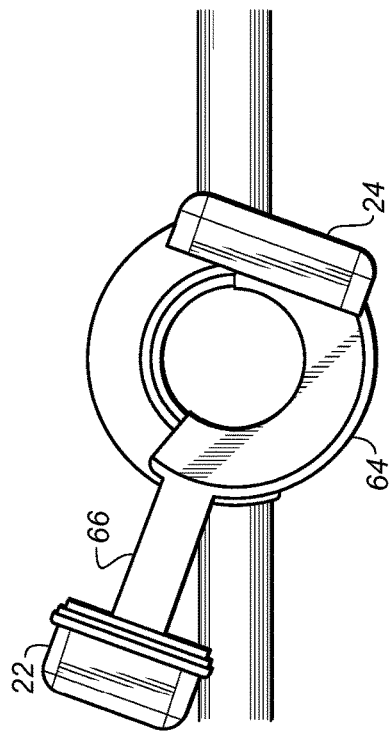
FIG. 16A is a perspective view of an exemplary source and detector orbital transport apparatus schematically illustrated in FIGS. 15A-B.
Figure 16B:
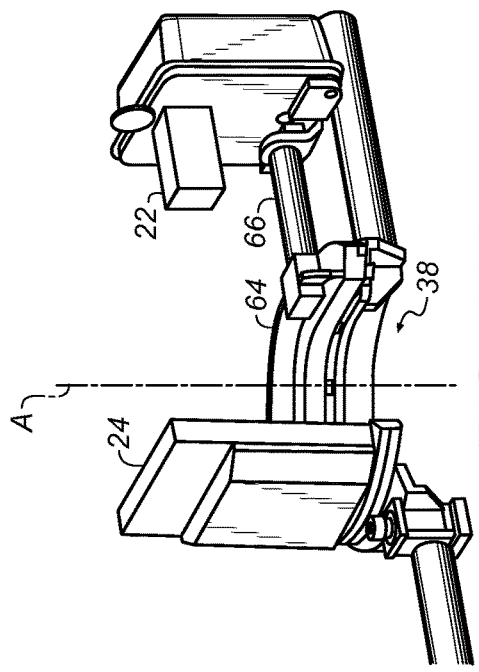
FIG. 16B is a top view of another exemplary orbital transport apparatus schematically illustrated in FIGS. 15A-B.
Figure 16C:
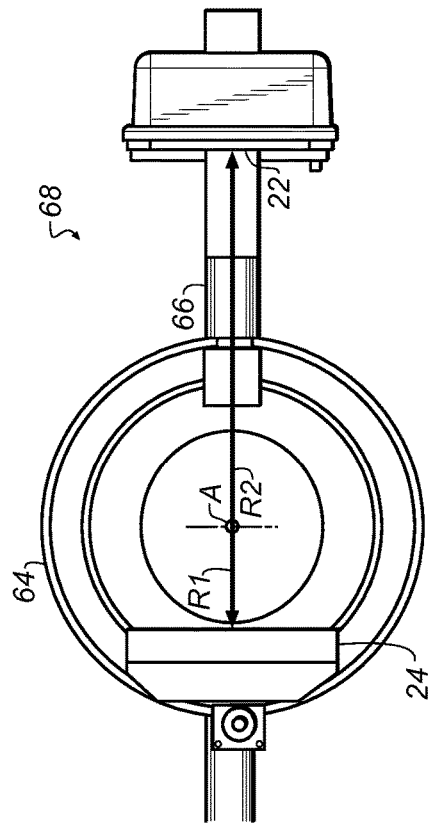
FIG. 16C is a top view of the exemplary orbital transport apparatus of FIG. 16B rotated to a different position.

With respect to FIGS. 16A-C, there is illustrated an embodiment of an orbital transport apparatus 68 illustrated schematically in FIGS. 15A-B. Such a configuration provides a source and detector transport using a single mechanical assembly having a rotating arm member 66, on a turntable 64, that is affixed to the detector 22, and that rotates about a central axis A and provides the different radii for the source R2, and for the detector R1. The rotating arm member 66 may be used to extend a radius R1 (and R2) of the source (or detector) as desired. As is shown in the perspective view of FIG. 16A, the source 22 and detector 24 may revolve around the C-shaped turntable 64, orbiting a subject animal limb positioned at central axis A. In this example, the source and detector may be revolved at less than 360 degrees. In the embodiment shown in FIG. 16B, the source 22 and detector 24 may ride along the surface of the O-shaped turntable 64, orbiting a subject animal limb positioned at central axis A. In this example, the source and detector may be revolved 360 degrees. FIG. 16C illustrates the source 22 and the detector revolved from the position shown in FIG. 16B. It should be emphasized that the embodiments shown using rotating arm member 66 on turntable 64 can be encased in one or more housings, thereby providing similar appearance to imaging systems described above. A portion or all of the source and detector components may extend through the top surfaces of the support bases disclosed herein.

In the imaging systems described herein, movement sensing may be optionally provided. This may be done in a number of ways. An optical camera may be used, according to an embodiment of the present invention, for determining whether or not movement of the animal during or before imaging may be excessive. Weight sensors, such as sensors embedded in the support base may be used to indicate weight-bearing condition for the subject extremity to be imaged and to indicate movement of the subject.

One or more platforms may be cooperatively coupled with the support base to support the animal. The platforms may be repositioned as needed according to the desired orientation of the subject for imaging. The platforms may be also covered with a heavy duty mat surface to help prevent slipping and provide a more comfortable surface. To allow ease of movement, platforms may be on casters, such as on spring-loaded, heavy duty casters. Walls may be provided with and without side panels. Walls may be provided with one or more access openings to allow access to source, detector, or the subject. An opening may slide or be hinged to allow access. The walls may be installed or positioned/re-positioned before or after the subject animal may be in position for the imaging session. Walls may be directly coupled to the support base. Walls may alternately be coupled to the control console.

Configurable guide rails may be provided to help in guidance and support, to provide structures for bindings, and to constrain movement of the subject. Guide rails may be removable and fitted into holes in the wall and other structures as needed. Fasteners may be provided to secure guide bars in place, with or without tools. Fasteners may be integral to the guide bars, such as captive bolts or clasps. Various types of restraint devices may be fitted around the animal, including foam inserts, air splints, bits, cross bars, or bindings, for example. This may include a bar that may be set in front of or between front or rear legs of the subject. A headrest may also be provided, allowing the animal to push against a surface to stabilize position or posture. A bar or other feature for resting against the chest, or receiving pressure from the subject along the chest, may also be useful.

Various types of hard or soft coverings may be provided for masking off one or more components of the extremity imaging scanning apparatus from the subject animal's field of view. Some amount of covering tends to alleviate animal anxiety from observing moving parts, for example. Coverings may serve a dual purpose, such as providing some measure of radiation shielding, for example. A chest rest bar may be provided separately or with the covering/apron/radiation shield. The chest rest bar may provide orientation for the animal, support for the horse to lean against, physical protection for a human handler (e.g., when used to guide or control the animal). In one embodiment, a structure may be configured to engage the chest of the horse with sufficient force for the horse to push against, extend horizontally (e.g., until outside the source path), drop vertically to be coupled to the support base. In one configuration, the drop to the support base may be angled, become wider or separate into divided sections (e.g., mounts or legs), implemented in stages or using a curved molded shape. Preferably the structure may be (a) sufficiently sized/wide/tall to hide the detector path and/or the source path from the animal, (b) to orient the animal, (c) sufficiently rigid/resistant to allow the animal to lean against, (d) sized to allow a handler to stand behind but in position to access the horse, (e) configured to provide radiation protection for a handler when equipped with a X-ray or radiation shield (e.g., apron), which may be integrated or attachable. In one embodiment, the structure may be attached to the support base, the platform or other part of the CBCT apparatus, or to the floor, wall or the like. In one embodiment, the structure may be configured to partially or fully encircle the horse's head/neck. In one embodiment, the structure may extend vertically to provide sufficient radiation protection to the human handler. In one embodiment, the structure may include a display or the like to provide information to the human handler such as an in-progress indicator that shows the time expended/remaining in an exposure. In one embodiment, the display on the structure may be a duplicate console to allow the technician to operate the CBCT apparatus from adjacent the structure. Other types of apron and curtain or draping may be used, draped over various parts of the animal and over equipment components.

Radiation shielding may be provided behind the detector and by a number of system components. Shielding may be integral to transport apparatus, walls, coverings, guide bars, tunnels, and other features. Additional shields may be designed and placed about or against the subject during imaging. Aprons, headgear, chest and arm protectors, gloves, boots, leggings, and protective pads may be provided for animal handlers and technicians who may need to support the animal during exposure. Interlocks may be provided to ascertain that protective gear has been donned by attending personnel. Interlocks may also be provided to verify that particular shielding structures may be in place. For example, an interlock may be provided to check that the operator console is behind the wall relative to the radiation source. The extremity imaging apparatus may be designed to allow various cleaning solutions to be used without damage to the equipment and allows hose cleaning. Disassembly of parts allows access for wiping down components and cleaning fittings.

The radiation source and detector may be temporarily disengaged from the support base to allow cleaning. Surfaces of the extremity imaging apparatus may be washable to allow regular cleaning. Various types of plastics or metals such as stainless steel may be used. According to an embodiment of the present invention, various components of the extremity imaging apparatus may be designed to fold down or break away when kicked. Magnets or other devices may be used to maintain components in position while allowing the needed amount of holding force/yield capability. The operator interface at the processor display console lists available exam types. Some variables may be allowed for specific exams or modalities. Among variables that may be changed by the operator may be starting and ending angles for orbit motion of source and detector. According to an embodiment, the operator display shows the relative angle of the source and detector when positioned in the track or slot of the support base. The display shows results with operator or actuator movement of the source or detector to a different angle.

A number of default positions may be set up according to the operator selection of an exam type. Initial positioning of imaging components places them at these default positions. Operator instructions may be provided for options on positioning and constraining the animal. Based on the exam type, the operator instructions may show the options available for the exam. The operator may set energy levels (kVp) and make other settings and adjustments to exposure-related parameters. The angular range and resolution may be set. The user interface allows exam initiation and termination. A trigger may be provided, removable from the operator console such as on a tether, for initiation of exposure. The operator interface screen displays results of 2-D projection images as they are captured, as well as the 3-D reconstructed image that may be generated. Various parameters related to the subject may be displayed and monitored during imaging, including heart rate, muscle tension, and other parameters. A touchscreen interface may be provided. Alternately, an optional keyboard and mouse may be used for command entry. The operator display screen may show a layout of the imaging apparatus with the area that may be irradiated during movement of the radiation source highlighted. This helps to indicate where shielding may be provided and where personnel access should be restricted to only those wearing protective gear. The detector and radiation source may be moved out of imaging position for leading the animal into the apparatus or exiting the imaging apparatus. Detents or other guides may be provided in order to obtain precise alignment. An operator interface command also permits a dry-run, allowing handler and other personnel to observe animal response, such as to movement of imaging devices. A calibration sequence may be provided for periodic recalibration of the detector. According to an embodiment of the present invention, at least one dry-run cycle may be provided, during which the source and detector orbit the subject, but without exposure. This enables the setup to be quickly evaluated and allows observation of the subject's response to component movement.

Consistent with at least one embodiment, exemplary methods/apparatus may use a computer program with stored instructions that perform on image data that may be accessed from an electronic memory. As may be appreciated by those skilled in the image processing arts, a computer program of an embodiment herein may be utilized by a suitable, general-purpose computer system, such as a personal computer or workstation. However, many other types of computer systems may be used to execute the computer program of described exemplary embodiments, including an arrangement of networked processors, for example.

The computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that may be connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, may refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that may be used as a temporary buffer or workspace by a microprocessor or other control logic processor device. Display data, for example, may be typically stored in a temporary storage buffer that may be directly associated with a display device and may be periodically refreshed as needed in order to provide displayed data. This temporary storage buffer may also be considered to be a memory, as the term may be used in the present disclosure. Memory may be also used as the data workspace for executing and storing intermediate and final results of calculations and other processing. Computer-accessible memory may be volatile, non-volatile, or a hybrid combination of volatile and non-volatile types.

It will be understood that computer program products for exemplary embodiments herein may make use of various image manipulation algorithms and processes that may be well known. It will be further understood that exemplary computer program product embodiments herein may embody algorithms and processes not specifically shown or described herein that may be useful for implementation. Such algorithms and processes may include conventional utilities that may be within the ordinary skill of the image processing arts. Additional aspects of such algorithms and systems, and hardware and/or software for producing and otherwise processing the images or co-operating with the computer program product of the application, may be not specifically shown or described herein and may be selected from such algorithms, systems, hardware, components and elements known in the art.

It should be noted that while the present description and examples are primarily directed to radiographic medical imaging of an animal or other subject, embodiments of apparatus and methods of the present application may also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems may utilize method and apparatus embodiments according to the application. As described herein, an exemplary planar panel DR detector/imager may be capable of both single shot (radiographic) and continuous (fluoroscopic) image acquisition. Further, a fan beam CT DR imaging system may be used.

Exemplary DR detectors may be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation. Exemplary embodiments according to the application may include various features described herein (individually or in combination).

While the invention has been illustrated with respect to one or more implementations, alterations and/or modifications may be made to the illustrated examples without departing from the spirit and scope of the appended claims. In addition, while a particular feature of the invention may have been disclosed with respect to only one of several implementations/embodiments, such feature may be combined with one or more other features of the other implementations/embodiments as may be desired and advantageous for any given or particular function. The term "at least one of" may be used to mean one or more of the listed items may be selected. The term "about" indicates that the value listed may be somewhat altered, as long as the alteration does not result in nonconformance of the process or structure to the illustrated embodiment. Finally, "exemplary" indicates the description may be used as an example, rather than implying that it may be an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An apparatus for radiographic imaging of an animal, the apparatus comprising:
   a support base having a top surface to support a four legged animal standing thereon;
   a moveable x-ray source disposed within a source housing and mechanically attached to the support base; and
   a digital radiographic detector mechanically attached to the support base, wherein the source housing and the detector extend upward substantially perpendicular to, and above, the top surface of the support base, and wherein the x-ray source and the detector are configured to capture a radiographic image of at least one foreleg or hind leg of the standing animal,
   wherein the source and the detector are attached to separate, concentric, moveable portions of the top surface of the support base, each of the moveable portions of the top surface of the support base comprising a ring shape coplanar with a plane of the top surface of the support base.

2. The apparatus of claim 1, wherein the source and the detector are configured to both revolve about said at least one foreleg or hind leg of the standing animal while capturing a plurality of radiographic images of said at least one foreleg or hind leg of the standing animal, and wherein a radius of a revolution path of the source is greater than a radius of a revolution path of the detector.

3. The apparatus of claim 2, wherein the source and the detector are configured to both revolve about said at least one foreleg or hind leg the standing animal by a motor control that is programmed with a start position for revolving about said at least one foreleg or hind leg the standing animal and a stop position for revolving about said at least one foreleg or hind leg the standing animal.

4. The apparatus of claim 2, wherein at least one of the source and the detector include a mechanism for increasing and decreasing the radius of its revolution path, the mechanism allowing at least one of the source and the detector to be moved further or closer to a central axis of the revolution path.

5. The apparatus of claim 2, further comprising a mechanism for raising and lowering the x-ray source and the detector such that the raising and lowering act to target a different portion of the at least one foreleg or hind leg of the standing animal for radiographic imaging.

6. The apparatus of claim 5, wherein the apparatus is configured such that the raising and lowering are performed simultaneously with revolving the source and the detector to perform a helical scan of the at least one foreleg or hind leg of the standing animal.

7. The apparatus of claim 2, further comprising a removable hood over at least one of the source and the detector to conceal movement of the source and detector.

8. The apparatus of claim 1, further comprising:
   a railing for guiding the animal into a position for capturing the radiographic image of the at least one foreleg or hind leg of the standing animal; and
   a flexible radiographic shield material configured to be draped over the railing to prevent scattering of radiographic energy emitted by the x-ray source.

9. The apparatus of claim 1, further comprising a hoof restraint disposed between the source and the detector, the hoof restraint comprising a pedestal for supporting a hoof of the animal during radiographic imaging of the hoof or its corresponding limb.

10. The apparatus of claim 9, wherein the hoof restraint comprises straps for securing the hoof to the pedestal.

11. The apparatus of claim 9, wherein the hoof restraint comprises a clamp made from a magnetizable metal, wherein the pedestal is made from a magnetizable metal, and wherein the hoof restraint further comprises a magnetic portion for securing the clamp to the pedestal.

12. The apparatus of claim 1, wherein the support base is sized such that one or more legs of the standing animal is supported by the support base and remaining legs of the animal are not supported by the support base.

13. The apparatus of claim 1, wherein the apparatus comprises a hardwired communication link to a processing system for controlling an imaging sequence of the at least one foreleg or hind leg of the standing animal and for receiving digital image data from the detector generated by the imaging sequence.

14. An apparatus for radiographic imaging of an animal, the apparatus comprising:
   a support base having a top surface to support a four legged animal standing thereon;

a moveable x-ray source disposed within a source housing and mechanically attached to the support base; and a digital radiographic detector mechanically attached to the support base, wherein the source housing and the detector extend upward substantially perpendicular to, and above, the top surface of the support base, and wherein the x-ray source and the detector are configured to capture a radiographic image of at least one foreleg or hind leg of the standing animal, wherein the support base comprises an orbital transport apparatus below the top surface of the support base, the source and the detector are attached to the orbital transport apparatus, and wherein the orbital transport apparatus is connected to the source and detector through slots in the top surface of the support base.

15. The apparatus of claim 14, further comprising a mechanism for lowering the source and the detector below the top surface of the support base through the slots in the top surface of the support base.

16. An apparatus for radiographic imaging of an animal, the apparatus comprising:

a support base having a top surface to support a four legged animal standing thereon;

a moveable x-ray source disposed within a source housing and mechanically attached to the support base;

a digital radiographic detector mechanically attached to the support base, wherein the source housing and the detector extend upward substantially perpendicular to, and above, the top surface of the support base, and wherein the x-ray source and the detector are configured to capture a radiographic image of at least one foreleg or hind leg of the standing animal; and a planar platform attached to the support base, the planar platform configured to support either the forelegs or the hind legs of the standing animal that are not being imaged, wherein the planar platform is positioned in a plane horizontally adjacent to the support base and is moveable in the plane about the support base to support the forelegs or the hind legs of the animal standing on the support base and on the platform, and to facilitate positioning of the animal relative to the source and detector for imaging different anatomical regions of the animal.

17. The apparatus of claim 16, further comprising a means for rotating the support base and the platform having the animal standing thereon while maintaining the source and the detector fixed in a stationary position.

18. The apparatus of claim 16, wherein the platform comprises a ramped incline for facilitating walking the animal onto the platform and the support base.

* * * * *